(12) United States Patent
Kim et al.

(10) Patent No.: US 12,285,607 B2
(45) Date of Patent: Apr. 29, 2025

(54) OPTIMAL STIMULATION POSITION COMBINATION DETERMINATION METHOD, SERVER, AND COMPUTER PROGRAM USING PRESET GUIDE SYSTEM

(71) Applicant: NEUROPHET Inc., Seoul (KR)

(72) Inventors: Dong Hyeon Kim, Seoul (KR); Bong Seok Ko, Seongnam-si (KR)

(73) Assignee: NEUROPHET Inc., Seoul (KR)

( * ) Notice: Subject to any disclaimer, the term of this patent is extended or adjusted under 35 U.S.C. 154(b) by 544 days.

(21) Appl. No.: 17/676,722

(22) Filed: Feb. 21, 2022

(65) Prior Publication Data

US 2023/0011442 A1 Jan. 12, 2023

(30) Foreign Application Priority Data

Jul. 6, 2021 (KR) .................. 10-2021-0088246

(51) Int. Cl.
*A61N 1/36* (2006.01)
*G16H 20/70* (2018.01)
*G16H 50/20* (2018.01)
*G16H 50/50* (2018.01)

(52) U.S. Cl.
CPC ..... *A61N 1/36031* (2017.08); *A61N 1/36025* (2013.01); *G16H 20/70* (2018.01); *G16H 50/50* (2018.01)

(58) Field of Classification Search
CPC ............ A61N 1/36031; A61N 1/36025; A61N 1/0456
See application file for complete search history.

(56) References Cited

U.S. PATENT DOCUMENTS

| | | | |
|---|---|---|---|
| 2016/0346164 A1* | 12/2016 | Ward | H04L 67/00 |
| 2019/0059732 A1* | 2/2019 | Kim | A61B 5/0042 |
| 2021/0023368 A1* | 1/2021 | Shakour | A61N 1/0456 |

FOREIGN PATENT DOCUMENTS

| | | |
|---|---|---|
| KR | 101758903 B1 | 7/2017 |
| KR | 1020180051750 A | 5/2018 |
| KR | 1020190028901 A | 3/2019 |
| KR | 1020200138111 A | 12/2020 |

* cited by examiner

*Primary Examiner* — Brian T Gedeon
(74) *Attorney, Agent, or Firm* — BROADVIEW IP LAW, PC

(57) ABSTRACT

Provided are an optimal stimulation position combination determination method using a preset guide system, a server, and a computer program. The optimal stimulation position combination determination method using a preset guide system according to various embodiments of the present invention is executed by a computing device and includes: simulating electric stimulation for a brain of a subject by using a plurality of stimulation position according to a preset guide system; and determining an optimal stimulation position combination for applying the electric stimulation to the preset target point in the brain of the subject by using a simulation result of the electric stimulation.

11 Claims, 14 Drawing Sheets

Optimization Report

[Conditions]
Target p[timize quantity : Enorm
Electrede max number : 8
Electrede shape : Disc 1 cm^2
Maximum current L 2.000

Target 1, Position : 279.30, 2.79, 327.86, Quantity amplitude : 0.104

[Result electrodes by 10-20 based optimization calculation]
Electrode 1 : Iz, Position : 256.97, -93.62, 347.00, amplitude : -0.800 mA
Electrode 2 : T9, Position : 178.25, 4.77, 348.96, amplitude : 0.100 mA
Electrode 3 : FT8, Position : 338.49, 32.90, 308.22, amplitude : -0.700 mA
Electrode 4 : P8, Position : 327.87, -53.02, 311.04, amplitude : -0.200 mA
Electrode 5 : F9, Position : 186.98, -63.16, 344.55, amplitude : 0.400 mA
Electrode 6 : FT9, Position : 180.82, 34.78, 347.25, amplitude : -0.300 mA
Electrode 7 : TP9, Position : 174.69, -20.29, 350.53, amplitude : 0.700 mA
Electrode 8 : F10, Position : 328.71, 62.43, 341.10, amplitude : 0.800 mA

OPTIMAL STIMULATION POSITION COMBINATION DETERMINATION METHOD, SERVER, AND COMPUTER PROGRAM USING PRESET GUIDE SYSTEM

CROSS-REFERENCE TO RELATED APPLICATION

This application is based on and claims priority under 35 U.S.C. 119 to Korean Patent Application No. 10-2021-0088246, filed on Jul. 6, 2021, in the Korean Intellectual Property Office, the disclosure of which is herein incorporated by reference in its entirety.

TECHNICAL FIELD

Various embodiments of the present invention provide an optimal stimulation position combination determination method using a preset guide system performed to apply electric stimulation to a target point preset to a brain of a subject, and a server and a computer program for determining an optimal stimulation position combination.

BACKGROUND ART

The brain is an internal organ of a human head and is the highest central organ of the nervous system and is divided into cerebrum, cerebellum, midbrain, pons, and medulla oblongata. In addition, the brain generates a brain wave which is a signal obtained by measuring a total sum of neuronal activity levels in an epidermis of the brain.

As a method for measuring a state of the brain, there are an EEG (electroencephalogram) test, which measures and examines the brain waves received from electrodes by attaching pads with electrodes to a scalp, a CT scan which examines the brain by taking tomography from various angles using radiation or ultrasound, an MRI scan which images the brain by magnetic resonance, and the like Various concepts are known in the field of neural stimulation of brain structures, and brain stimulation which stimulates the brain to achieve a predetermined purpose is largely classified into invasive brain stimulation and non-invasive brain stimulation.

The invasive brain stimulation is a method in which electrodes are inserted into the brain through surgery and electrical signals are applied, and the non-invasive brain stimulation is a method in which a predetermined effect is achieved by stimulating the brain without inserting the electrodes inside a skull.

Specific brain stimulation includes deep electric stimulation, transcranial magnetic stimulation (TMS), transcranial electric stimulation (TES), transcranial direct current stimulation (tDCS), and transcranial random noise stimulation (tRNS).

Among these brain stimulations, a brain electric stimulation technology using the transcranial direct current stimulation (tDCS) is one of the relatively simple non-invasive brain stimulations that is known to be able to improve cognitive abilities or to be effective in treating various cranial nerve diseases such as depression, attention deficit hyperactivity disorder (ADHD), epilepsy, dementia, and sleep disorders, and thus, the brain stimulations are actively studied.

In the method for stimulating the brain by using the transcranial direct current stimulation (tDCS) device, an anode and a cathode are connected to a transcranial direct current stimulation (tDCS) device that generates a direct current, and when a current is injected into the anode, the current passes through the cerebrum and comes back into the cathode.

In this case, the current flows from the anode to the cathode to stimulate the cerebrum, and it may be necessary to change the direction of the electric stimulation according to the treatment method.

On the other hand, the transcranial direct current stimulation has a problem in that, since the user directly selects the positions to be attached with the electrodes and attaches the electrodes to the selected positions, it cannot accurately be recognized that the positions of the electrodes selected by the user are the positon that can accurately stimulate target points of the brain, that is, the points of the brain to which the electric stimulation is to be applied.

In addition, there is a problem in that, even if the position selected by the user is the position that can accurately stimulate the target point in the brain, it is difficult to accurately attach the electrode to the position selected by the user, in particular, it is very difficult to repeatedly attach the electrode to the same position in order to repeatedly apply the same stimulation.

SUMMARY OF INVENTION

Technical Problem

An object of the present invention is to provide an optimal stimulation position combination determination method, server, and computer program using a preset guide system that are capable of accurately applying electric stimulation to a target point and that are capable of determining and guiding an optimal stimulation position combination so as to minimize side effects by reducing influence exerted to other nearby points by simulating the electric stimulation for a brain of a subject by using a plurality of stimulation positions according to the preset guide system (for example, a 10-20 system) and determining an optimal stimulation position combination for applying the electric stimulation to a preset target point in the brain of the subject by using a simulation result of the electric stimulation.

Another object of the present invention is to provide an optimal stimulation position combination determination method using a preset guide system, server, and computer program that are capable of providing the optimal stimulation position combination applicable to various types of transcranial direct current stimulation devices with different numbers of electrodes and that are capable of deriving maximum efficiency with the limitative number of electrodes by determining the optimal stimulation position combination that can accurately apply electric stimulation to a target point preset to a brain of a subject and by correcting the optimal stimulation position combination based on the number of electrodes included in a transcranial direct current stimulation device used by a user, that is, the number of available electrodes.

Still another object the present invention is to provide an optimal stimulation position combination determination method using a preset guide system, server, and computer program that is capable of determining the optimal stimulation position combination determined in consideration of only the stimulation position to which the electric stimulation can be accurately applied with the electrodes being actually attached by determining the optimal stimulation position combination to which the electric stimulation to the target point preset to the brain of the subject can be accurately applied by filtering the stimulation positions to which the electric stimulation cannot accurately be applied since the electrode attachment cannot be made due to physical features or disease, wound, or the like occurring in the head of the subject.

The objects of the present invention are not limited to the object mentioned above, and other objects not mentioned will be clearly understood from the following description by the ordinarily skilled in the art.

Solution to Problem

According to an embodiment, there is provided an optimal stimulation position combination determination method performed by a computing device using a preset guide system to apply electric stimulation to a target point preset to a brain of a subject, including: simulating the electric stimulation for the brain of the subject by using a plurality of stimulation positions according to the preset guide system; and determining an optimal stimulation position combination for applying the electric stimulation to the preset target point based on a simulation result of the electric stimulation.

In various embodiments, the simulating the electric stimulation may include: generating a three-dimensional brain map corresponding to the brain of the subject; and simulating the electric stimulation by using the plurality of stimulation positions based on the generated three-dimensional brain map.

In various embodiments, the generating the three-dimensional brain map may include: acquiring an MRI image of the brain of the subject; segmenting the acquired MRI image into a plurality of regions; generating a three-dimensional brain image by using the MRI image segmented into the plurality of regions; and generating the three-dimensional brain map configured with a plurality of meshes based on an attribute of each of the plurality of regions included in the generated three-dimensional brain image.

In various embodiments, the determining the optimal stimulation position combination includes may include: setting the number of maximum stimulation positions at which the electric stimulation is applied to the preset target point, and correcting the determined optimal stimulation position combination by comparing the number of the optimal stimulation positions included in the determined optimal stimulation position combination with the number of the set maximum stimulation positions.

In various embodiments, the correcting the determined optimal stimulation position combination may include: selecting at least one of the plurality of optimal stimulation positions based on importance of each of the plurality of optimal stimulation positions, in a case where the number of the plurality of optimal stimulation positions included in the determined optimal stimulation position combination exceeds the number of the set maximum stimulation positions, wherein the number of the selected at least one optimal stimulation position is less than or equal to the number of the set maximum stimulation positions; and simulating the electric stimulation by using only the selected at least one optimal stimulation position and correcting the determined optimal stimulation position combination based on a simulation result of the electric stimulation by using only the selected at least one optimal stimulation position.

In various embodiments, the optimal stimulation position combination determination method may further include providing information on the determined optimal stimulation position combination in a case where the number of the plurality of optimal stimulation positions included in the determined optimal stimulation position combination is less than or equal to the number of the set maximum stimulation positions.

In various embodiments, the determining the optimal stimulation position combination may include: standardizing a plurality of current values applied to each of the plurality of optimal stimulation positions included in the determined optimal stimulation position combination based on a preset current resolution; primarily correcting each of the plurality of standardized current values so that each of the plurality of standardized current values is a multiple of the preset current resolution; and secondarily correcting at least one current value of the plurality of primarily-corrected current values based on a total sum of the plurality of primarily-corrected current values.

In various embodiments, the secondarily correcting may include: selecting at least one optimal stimulation position among the plurality of optimal stimulation positions based on importance of each of the plurality of optimal stimulation positions in a case where the total sum of the plurality of primarily-corrected current values is not 0 and determining the number of the selected at least one optimal stimulation positions according to a magnitude of the total sum of the plurality of primarily-corrected current values; and secondarily correcting the primarily-corrected current values corresponding to the selected at least one optimal stimulation position so that the total sum of the plurality of primarily-corrected current values is 0.

In various embodiments, the determining the optimal stimulation position combination may further include providing information on the determined optimal stimulation position combination including a value obtained by multiplying each of the plurality of primarily-corrected current values by the preset current resolution in a case where the total sum of the plurality of primarily-corrected current values is 0.

In various embodiments, the simulating the electric stimulation may include: filtering stimulation positions corresponding to a preset condition among the plurality of stimulation positions; and simulating the electric stimulation for the brain of the subject by using remaining stimulation positions except for the filtered stimulation positions among the plurality of stimulation positions.

According to another embodiment of the present invention, there is provided an optimal stimulation position combination determination server using a preset guide system, including: a processor; a network interface; a memory; and a computer program loaded on the memory and executed by the processor, wherein the computer program includes: an instruction of simulating electric stimulation for a brain of a subject by using a plurality of stimulation positions according to the preset guide system; and an instruction of determining an optimal stimulation position combination for applying the electric stimulation to a preset target point in the brain of the subject based on a simulation result of the electric stimulation.

According to still another embodiment of the present invention, there is provided a computer program recorded on a computer-readable recording medium combined with a computing device and causing the computing device to execute: simulating electric stimulation for a brain of a subject by using a plurality of stimulation position according to a preset guide system; and determining an optimal stimulation position combination for applying the electric stimulation to the preset target point in the brain of the subject by using a simulation result of the electric stimulation.

Other specific details of the present invention are included in the detailed description and the drawings.

Advantageous Effects of Invention

According to various embodiments of the present invention, it is possible to obtain an advantage of being capable of accurately applying electric stimulation to a target point and being capable of determining and guiding an optimal stimulation position combination so as to minimize side effects by reducing influence exerted to other nearby points by simulating the electric stimulation for a brain of a subject by using a plurality of stimulation positions according to the preset guide system (for example, a 10-20 system) and determining an optimal stimulation position combination for applying the electric stimulation to a preset target point in the brain of the subject by using a simulation result of the electric stimulation.

In addition, it is possible to obtain an advantage of being capable of providing the optimal stimulation position combination applicable to various types of transcranial direct current stimulation devices with different numbers of electrodes and being capable of deriving maximum efficiency with the limitative number of electrodes by determining the optimal stimulation position combination that can accurately apply electric stimulation to a target point preset to a brain of a subject and by correcting the optimal stimulation position combination based on the number of electrodes included in a transcranial direct current stimulation device used by a user, that is, the number of available electrodes.

In addition, it is possible to obtain an advantage of being capable of improving a speed of determining the optimal stimulation position combination by reducing unnecessary calculations in the process of performing the simulation and being capable of determining the optimal stimulation position combination determined in consideration of only the stimulation position to which the electric stimulation can be accurately applied with the electrodes being actually attached by determining the optimal stimulation position combination to which the electric stimulation to the target point preset to the brain of the subject can be accurately applied by filtering the stimulation positions to which the electric stimulation cannot accurately be applied since the electrode attachment cannot be made due to physical features or disease, wound, or the like occurring in the head of the subject.

Effects of the present invention are not limited to the effects mentioned above, and other effects not mentioned will be clearly understood from the following description by those skilled in the art.

BRIEF DESCRIPTION OF DRAWINGS

FIGS. 17 and 18 are diagrams exemplarily illustrating a third UI provided by the optimal stimulation position combination determination server using the preset guide system in various embodiments.

DESCRIPTION OF EMBODIMENTS

Figure 1:
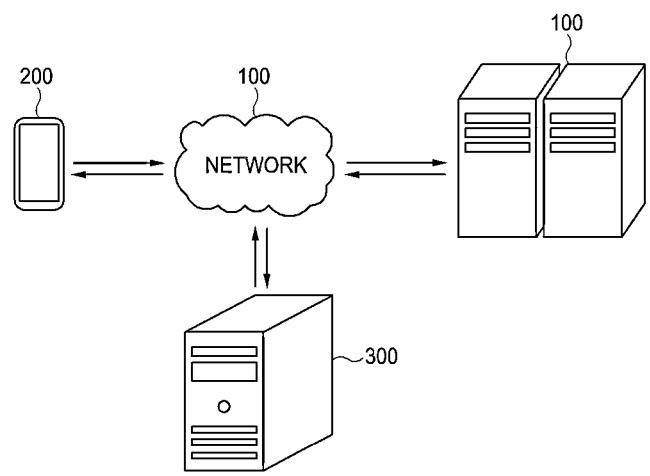
FIG. 1 is a diagram illustrating an optimal stimulation position combination determination system using a preset guide system according to an embodiment of the present invention.

Advantages and features of the present invention and methods of achieving the advantages and features will become apparent with reference to embodiments described below in detail in association with the accompanying drawings. However, the present invention is not limited to the embodiments disclosed below, but the present invention can be implemented in various different forms, only the embodiments allow the disclosure of the present invention to be complete, the present invention is provided in order for the ordinarily skilled in the art to which the present invention belongs to fully understand the scope of the present invention, and the present invention is only defined by the scope of the claims.

The terminology used herein is for the purpose of describing the embodiments and is not intended to limit the present invention. In this specification, a singular form also includes a plural form unless a phrase specifically states otherwise. As used in this specification, "comprises" and/or "comprising" does not exclude the presence or addition of one or more other components in addition to the stated components. Throughout the specification, the same or similar reference numerals refer to the same or similar elements, and "and/or" includes each and all combination of one or more of the stated elements. Although "first", "second", and the like are used to describe various elements, of course, these elements are not limited by these terms. These terms are only used to distinguish one component from other components. Accordingly, it goes without saying that a first component mentioned below may be a second component within the spirit of the present invention.

Unless otherwise defined, all terms (including technical and scientific terms) used herein may be used with the meaning commonly understood by the ordinarily skilled in the art to which the present invention belongs. In addition, terms defined in a commonly used dictionary are not to be interpreted ideally or excessively unless specifically defined explicitly.

As used in this specification, the term "unit" or "module" refers to a software component or a hardware component such as FPGA or ASIC, and the "unit" or "module" performs a certain role. However, the "unit" or "module" is not meant to be limited to software or hardware. The "unit" or "module" may be configured to reside on an addressable storage medium or may be configured to reproduce one or more processors. Accordingly, as an example, the "unit" or "module" includes components such as software components, object-oriented software components, class components and task components, processes, functions, attributes, procedures, subroutines, segments of program codes, drivers, firmware, microcode, circuits, data, database, data structures, tables, arrays, and variables. The components and functions provided within the "unit" or "module" may be combined into a smaller number of components and "units" or "modules" or may be further separated in to additional components and "units" or "modules".

Spatially relative terms "below", "beneath", "lower", "above", "upper", and the like can be used to easily describe the relationship between a certain component and other components. Spatially relative terms should be understood as terms that include different directions of components during use or operation in addition to the directions illustrated in the drawings. For example, in a case where a component illustrated in the drawings is turned over, a component described as "below" or "beneath" of the other component may be placed "above" of the other component. Accordingly, the exemplary term "below" may include both directions below and above. Components may also be oriented in other orientations, and thus, spatially relative terms may be interpreted according to orientation.

In this specification, a computer denotes all types of hardware devices including at least one processor and may be understood as collectively including software configurations operating in a corresponding hardware device according to embodiments. For example, a computer may be understood as meaning including all of a smartphone, a tablet PC, a desktop, a notebook, and a user client and an application running in each device, but the present invention is not limited thereto.

Hereinafter, an embodiment of the present invention will be described in detail with reference to the accompanying drawings.

Each step described in this specification is described as being performed by a computer, but the subject of each step is not limited thereto, and at least a portion of each step may be performed in different devices according to embodiments.

FIG. 1 is a diagram illustrating an optimal stimulation position combination determination system using a preset guide system according to the embodiment of the present invention.

Referring to FIG. 1, the optimal stimulation position combination determination system using the preset guide system according to the embodiment of the present invention can include an optimal stimulation position combination determination server 100 (hereinafter, a "server 100"), a user terminal 200, and an external server 300.

Herein, the optimal stimulation position combination determination system using the preset guide system illustrated in FIG. 1 is different according to an embodiment, and components of the embodiment are not limited to the embodiment illustrated in FIG. 1, and the components can be added, changed, or deleted as necessary.

In one embodiment, the server 100 can determine an optimal stimulation position combination for applying electric stimulation to a preset target point of a brain of a subject (for example, a patient) according to transcranial direct current stimulation (tDCS) and can provide information on the determined optimal stimulation position combination, so that the subject or a user who intends to perform the transcranial direct current stimulation on the subject can be allowed to attach an electrode to an appropriate position and perform the electric stimulation.

In various embodiments, the server 100 can simulate the electric stimulation for the brain of the subject based on the preset guide system that defines the plurality of stimulation positions for the brain of the subject so as to perform the transcranial direct current stimulation, can determine the optimal stimulation position combination so as to accurately apply the electric stimulation to a specific target point based on a simulation result, and can provide information on the determined optimal stimulation position combination.

At this time, the information on the optimal stimulation position combination determined and provided according to the above-mentioned method can include information on an electrode attachment position that allows the electric stimulation to be accurately applied to the preset target point in the brain of the subject and can include information on how much the current value and for how long (that is, the current value, current application time, or the like) is to be applied, but the present invention is not limited thereto.

In various embodiments, the server 100 can be connected to the user terminal 200 through the network 400, and an optimal stimulation position combination determination service using the preset guide system and a service for providing information on the optimal stimulation position combination determined by using the optimal stimulation position combination determination service can be provided. In this case, the service provided by the server 100 can be implemented and provided in the form of a web or an application, but the present invention is not limited thereto.

Figure 12:
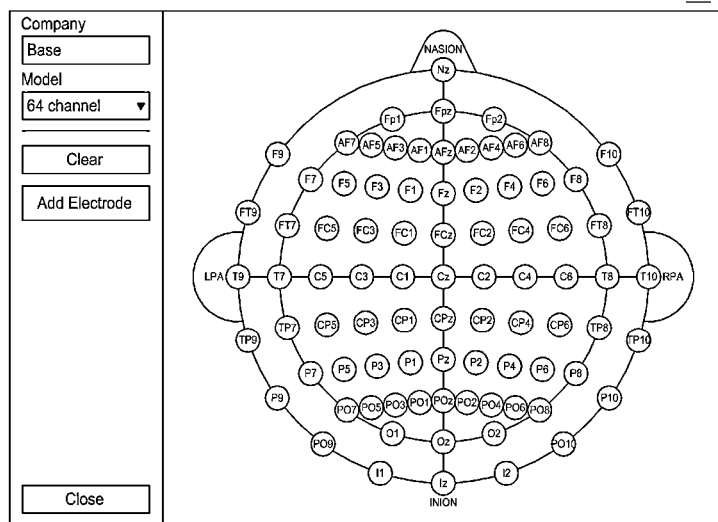
FIG. 12 is a diagram exemplarily illustrating a first user interface (UI) provided by the optimal stimulation position combination determination server using a preset guide system in various embodiments.
Figure 14:
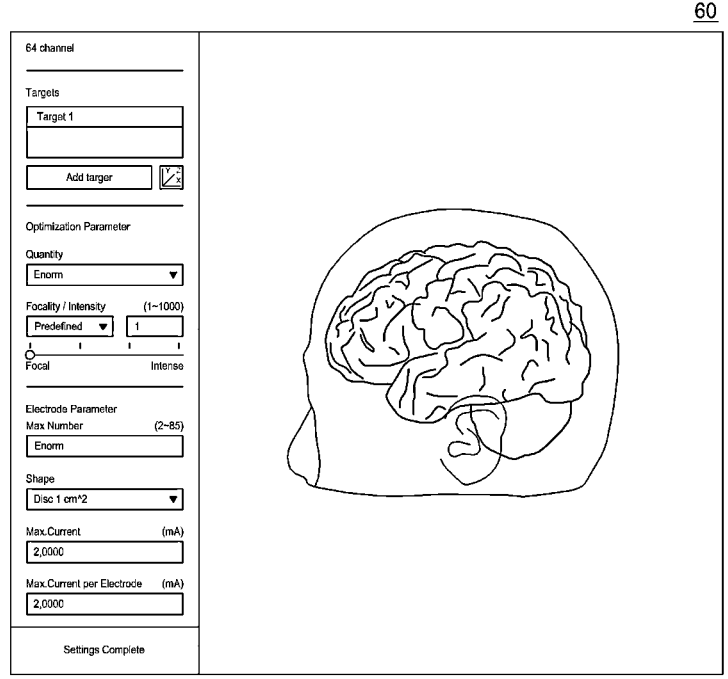
FIGS. 14 and 15 are diagrams exemplarily illustrating a second UI provided by the optimal stimulation position combination determination server using the preset guide system in various embodiments.
Figure 17:
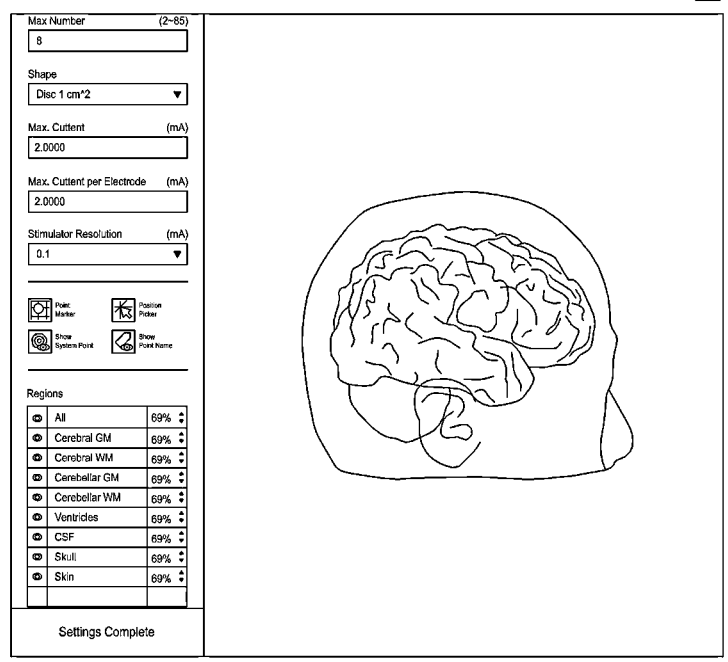

Herein, the user terminal 200 may include an operating system capable of driving an application in order to execute an application-type service provided by the server 100 and may be a smartphone including a display in a predetermined region in order to output an UI (for example, a first UI 50 of FIG. 12, a second UI 60 of FIGS. 14 and 15, and a third UI 70 of FIGS. 17 and 18) provided by the server 100, but the present invention is not limited thereto, and the user terminal 200 is a wireless communication device that guarantees portability and mobility and can include all types of hand-held-based wireless communication devices such as navigations, personal communication systems (PCS), global systems for mobile communications (GSM), personal digital cellular (PDC), personal hand phone system (PHS), personal digital assistant (PDA), international mobile telecommunication (IMR)-2000, CDMA (code division multiple access)-2000, W-code division multiple access (W-CDMA), wireless broadband internet (Wibro) terminal, smartpads, tablet PCs, and the like.

In addition, herein, the network 400 can denote a connection structure in which information exchange is possible between nodes such as a plurality of terminals and servers. For example, the network 400 can include a local region network (LAN), a wide region network (WAN), the Internet (WWW), a wired/wireless data communication network, a telephone network, a wired/wireless television communication network, and the like.

In addition, herein, the wireless data communication network includes 3G, 4G, 5G, third generation partnership project (3GPP), fifth generation partnership project (5GPP), long term evolution (LTE), world interoperability for microwave access (WIMAX), Wi-Fi, Internet, local area network (LAN), wireless local area network (LAN), wide area network (WAN), personal area network (PAN), radio frequency (RF), Bluetooth network, near-field communication (NFC) network, satellite broadcast network, analog broadcast network, digital multimedia broadcasting (DMB) networks, and the like, but the present invention is not limited thereto.

In one embodiment, the external server 300 can be connected to the server 100 via the network 400, and various information and data (for example, pre-computation information, calculation model for simulation, or the like) required in order for the server 100 to perform the optimal stimulation position combination determination method using the preset guide system can be provided, and various information and data generated when the server 100 performs the optimal stimulation position combination determination method using the preset guide system can be provided, stored, and managed.

In various embodiments, the external server 300 can be a storage server separately provided outside of the server 100, but the present invention is not limited thereto. Hereinafter, a hardware configuration of the server 100 performing the optimal stimulation position combination determination method using the preset guide system will be described with reference to FIG. 2.

Figure 2:
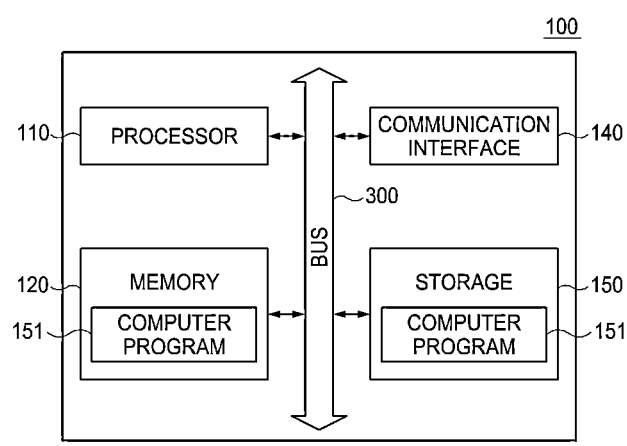
FIG. 2 is a hardware configuration diagram of an optimal stimulation position combination determination server using a preset guide system according to another embodiment of the present invention.

FIG. 2 is a hardware configuration diagram of the optimal stimulation position combination determination server using the preset guide system according to another embodiment of the present invention.

Referring to FIG. 2, In various embodiments, the server 100 can include one or more processors 110, a memory 120 for loading a computer program 151 executed by the processor 110, a bus 130, a communication interface 140, and a storage 150 for storing a computer program 151. Herein, only the components related to the embodiment of the present invention are illustrated in FIG. 2. Accordingly, one of the ordinarily skilled in the art to which the present invention belongs can understand that other general-purpose components other than components illustrated in FIG. 2 can be further included.

The processor 110 controls the overall operations of the components of the server 100. The processor 110 is configured to include a central processing unit (CPU), a micro controller unit (MPU), a graphic processing unit (GPU), or any type of processor well known in the art.

In addition, the processor 110 can perform an operation for at least one application or program for executing the method according to the embodiments of the present invention, and the server 100 can include one or more processors.

In various embodiments, the processor 110 can further include a random access memory (RAM, not illustrated) and a random access memory (ROM, not illustrated) that temporarily and/or permanently store signals (or data) processed inside the processor 110. In addition, the processor 110 can be implemented in a form of a system on chip (SoC) including at least one of a graphic processing unit, a RAM, and a ROM.

The memory 120 stores various data, commands and/or information. The memory 120 can load the computer program 151 from the storage 150 to execute methods/operations according to various embodiments. When the computer program 151 is loaded on the memory 120, the processor 110 can perform the method/operations by executing one or more instructions constituting the computer program 151. The memory 120 can be implemented as a volatile memory such as a RAM, but the technical scope of the present disclosure is not limited thereto.

The bus 130 provides a communication function between the components of the server 100. The bus 130 can be implemented as various types of buses, such as an address bus, a data bus, and a control bus.

The communication interface 140 supports wired/wireless Internet communication of the server 100. In addition, the communication interface 140 can support various communication methods other than the Internet communication. To this end, the communication interface 140 can be configured to include a communication module well known in the art of the present invention. In some embodiments, the communication interface 140 can be omitted.

The storage 150 can non-temporarily store the computer program 151. In the case of performing the optimal stimulation position combination determination process using the guide system preset through the server 100, the storage 150 can store various necessary information to provide the optimal stimulation position combination determination process using the preset guide system.

The storage 150 may be configured to include a non-volatile memory such as a read only memory (ROM), an erasable programmable ROM (EPROM), an electrically erasable programmable ROM (EEPROM), or a flash memory, a hard disk, a removable disk, or a well-known arbitrary-form computer-readable recording medium in the art to which the present invention belongs.

The computer program 151 can include one or more instructions that cause the processor 110 to perform methods/operations according to various embodiments of the present invention when the computer program 151 is loaded on the memory 120. That is, the processor 110 can perform the method/operations according to various embodiments of the present invention by executing the one or more instructions.

In one embodiment, the computer program 151 can include one or more instructions so as to be allowed to perform the optimal stimulation position combination determination method using the preset guide system including simulating the electric stimulation for the brain of the subject by using the plurality of stimulation positions according to the preset guide system and determining the optimal stimulation position combination for applying the electric stimulation to the preset target point to the brain of the subject based on the result of simulating the electric stimulation.

In addition, the computer program 151 can include one or more instructions so as to be allowed to perform the electric stimulation simulation method for determining the optimal stimulation position combination including filtering the stimulation positions corresponding to the preset condition among the plurality of stimulation positions according to the preset guide system and simulating the electric stimulation for the brain of the subject by using the remaining stimulation positions except for the filtered stimulation position among the plurality of stimulation positions.

Steps of a method or algorithm to be described with respect to the embodiment of the present invention, can be implemented directly in hardware or can be implemented as a software module executed by hardware, or by a combination thereof. A software module can reside on a random access memory (RAM), a read only memory (ROM), an erasable programmable ROM (EPROM), an electrically erasable programmable ROM (EEPROM), a flash memory, a hard disk, a detachable disk, a CD-ROM, or an arbitrary type of computer-readable recording medium well known in the art to which the present invention belongs.

The components of the present invention can be implemented as a program (or application) to be executed in combination with a computer as hardware and to be stored in a medium. The components of the present invention can be implemented as software programming or software components, and similarly, embodiments can include various algorithms implemented as data structures, processes, routines, or combinations of other programming components, and can be implemented in a programming or scripting language such as C, C++, Java, or assembler. Functional aspects can be implemented in an algorithm executed on one or more processors. Hereinafter, the optimal stimulation position combination determination method using the preset guide system performed by the server 100 will be described with reference to FIGS. 3 to 18.

Figure 3:
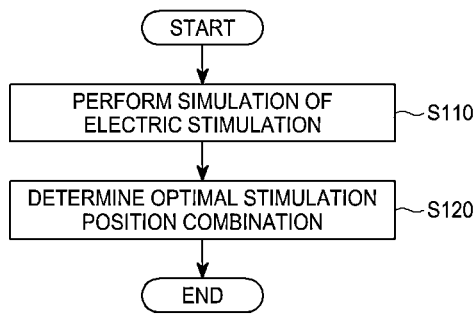
FIG. 3 is a flowchart of an optimal stimulation position combination determination method using a preset guide system according to still another embodiment of the present invention.

FIG. 3 is a flowchart of the optimal stimulation position combination determination method using the preset guide system according to another embodiment of the present invention.

Referring to FIG. 3, in step S110, the server 100 can simulate the electric stimulation for the brain of the subject by using the plurality of stimulation positions according to the preset guide system.

Figure 8:
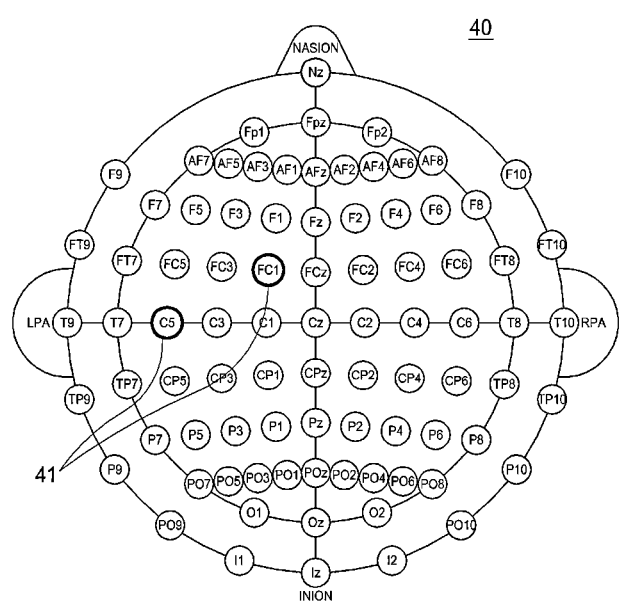
FIG. 8 is a diagram exemplarily illustrating a form in which the optimal stimulation position combination is determined among the plurality of stimulation positions according to a 10-20 system in various embodiments.

Herein, the preset guide system can denote a system that defines the plurality of stimulation positions for the brain of the subject in advance to guide the transcranial direct current stimulation and guides the electrode attachment positions to apply the electric stimulation to the target point of the brain accordingly. For example, as illustrated in FIG. 8, the preset guide system may be an EEG measurement 10-20 system 40 according to the international 10-20 system standard electrode attachment method, and the plurality of stimulation positions may denote positions where a plurality of EEG measurement channels (19, 24, 68, 128, or 256 caps or individual electrodes) are attached to the head of the subject according to the 10-20 system, but the present invention is not limited thereto.

In various embodiments, the server 100 can generate a three-dimensional brain map corresponding to the brain of the subject and can simulate the electric stimulation by using the plurality of stimulation positions based on the generated three-dimensional brain map. Hereinafter, the description will be made with reference to FIGS. 4 to 7.

Figure 4:
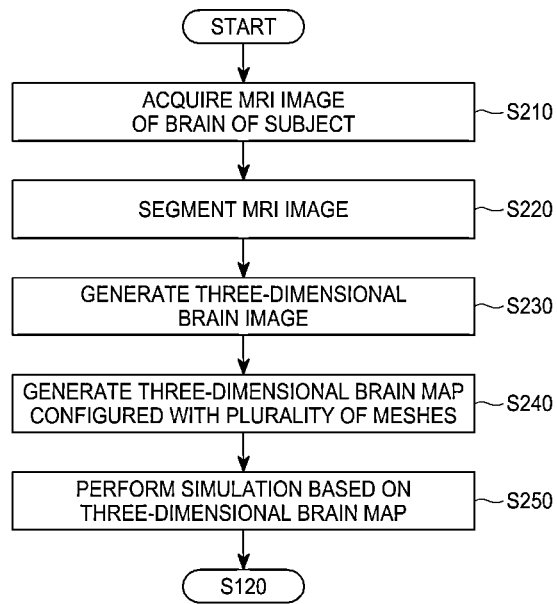
FIG. 4 is a flowchart illustrating a method for simulating electric stimulation by using a three-dimensional brain map in various embodiments.
Figure 5:
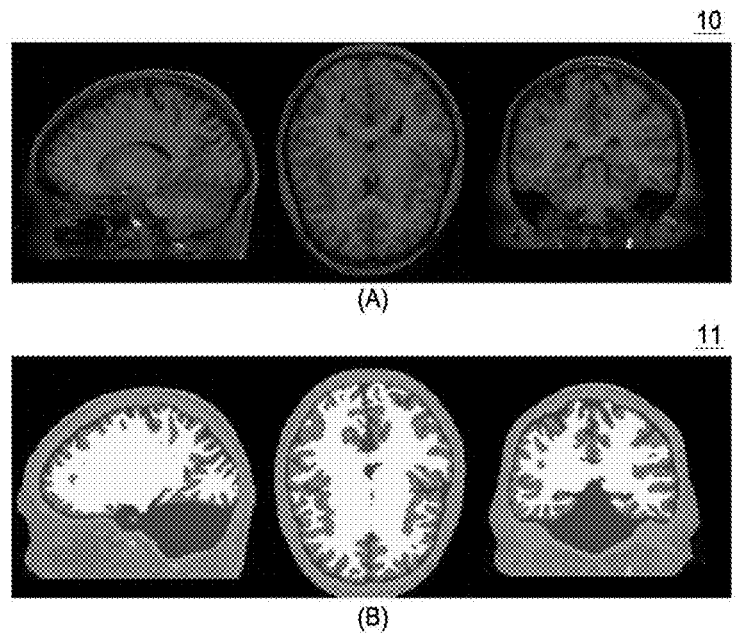
FIG. 5 is a diagram exemplarily illustrating an MRI image of a brain of a subject and a segmentation result of the MRI image according to various embodiments.

FIG. 4 is a flowchart illustrating a method for simulating the electric stimulation based on the three-dimensional brain map in various embodiments.

Referring to FIG. 4, in step S210, the server 100 can acquire a magnetic resonance imaging (MRI) image (for example, 10 of FIG. 5(A)) of the brain of the subject.

Herein, the MRI image of the brain of the subject can denote the MRI head image including the brain of the subject. That is, the MRI image of the brain of the subject can include the skull and the scalp of the subject as well as the brain of the subject. For example, the server 100 can be connected to a computer that is a workstation connected to an MRI image acquisition device and can directly acquire the MRI image of the brain of the subject from the MRI image acquisition device through the computer. However, the present invention is not limited thereto.

In step S220, the server 100 can segment (partition) the MRI image obtained in step S210 into the plurality of regions (for example, 11 in FIG. 5(B)).

In various embodiments, the server 100 can generate the plurality of regions by analyzing the acquired MRI image and segmenting the MRI image into images for regions of the brain. For example, the server 100 can segment the MRI image into images for a white matter region, a gray matter region, a cerebrospinal fluid region, a skull region, and a scalp region of the brain, but the present invention is not limited thereto.

In various embodiments, the server 100 can segment the MRI image into the plurality of regions by analyzing the MRI images with a previously learned artificial intelligence model.

Herein, the previously learned artificial intelligence model can include one or more batch normalization layers, activation layers, and convolution layers and can be an artificial intelligence model (for example, a model learned by using machine learning, in particular, a model learned by using deep learning) learned according to a machine-learning-based learning method with the MRI image segmented into the plurality of regions according to brain regions being set to a training data.

In addition, the previously learned artificial intelligence model can be configured to include a horizontal pipeline configured with a plurality of blocks for extracting high-level features from low-level features of the MRI image and a vertical pipeline for performing segmentation by collecting the features extracted with the horizontal pipeline and to perform segmentation on the MRI image having a relatively poor quality, but the present invention is not limited thereto.

In various embodiments, the server 100 can post-process the MRI image segmented into the plurality of regions according to the above-described method.

Figure 6:
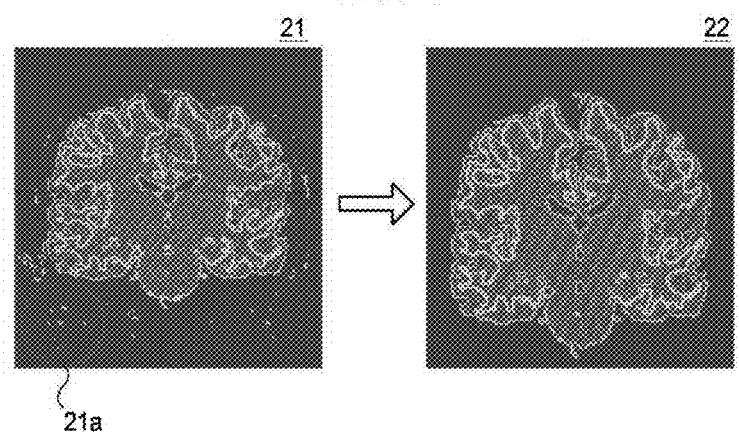
FIG. 6 is a diagram illustrating a process of removing noise from the MRI image segmented into a plurality of regions by performing connected-component-based noise removal according to various embodiments.

First, referring to FIG. 6, the server 100 can perform connected component-based noise rejection on the MRI image segmented into the plurality of regions.

Herein, the connected component-based noise rejection can be utilized in the process of improving the result of the MRI image segmentation performed by using a convolutional neural network (CNN). For example, in the MRI image 21 segmented into the plurality of regions as illustrated in FIG. 6, the server 100 removes remaining components 21a except for the connection component which is the largest chunk so that the server 100 can generate the MRI image 22 from which noise is removed.

Herein, various technologies are known in relation to a method for performing the connection component-based noise rejection, and these various known technologies can be selectively applied according to the circumstances, so that, in this specification, the connection component-based noise rejection method performed by the server 100 is not specifically disclosed.

Figure 7:
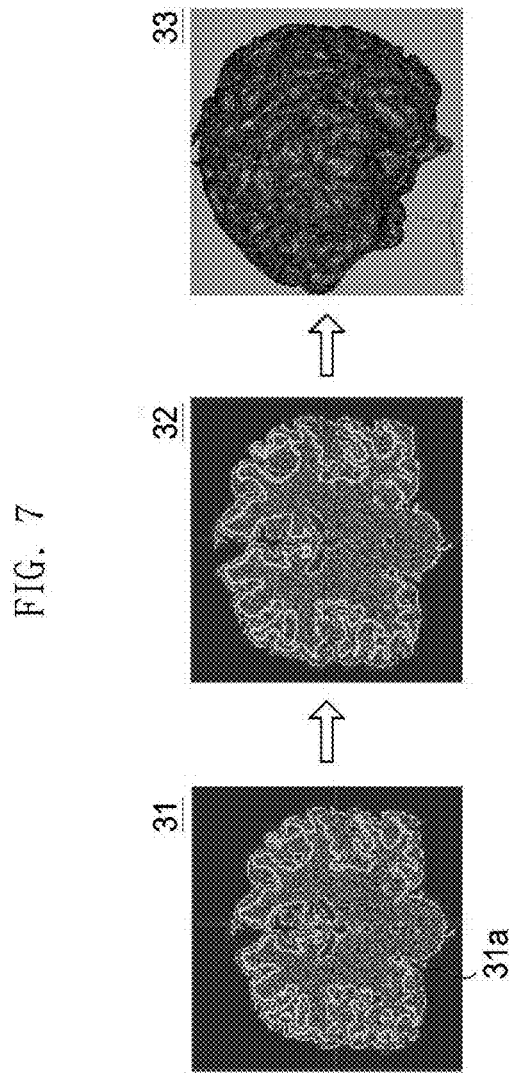
FIG. 7 is a diagram illustrating a process of generating a three-dimensional brain image by performing hole rejection on the MRI image segmented into the plurality of regions and by using the hole-rejection according to various embodiments.

After that, referring to FIG. 7, the server 100 can perform hole rejection on the MRI image segmented into the plurality of regions. Herein, the hole rejection can be utilized in removing a hole, which is one of errors in convolutional neural network-based segmentation. For example, the server 100 can generate the hole-removed MRI image 32 by removing at least a portion of the hole 31A included in the MRI image 31 segmented into the plurality of regions.

Herein, similarly to the method for performing the connection element-based noise rejection, various technologies are known in relation to a method for performing the hole rejection, and these various known technologies can be selectively applied according to circumstances, so that, in this specification, the method for performing hole rejection performed by the server 100 is not specifically disclosed.

In step S230, the server 100 can generate the three-dimensional brain image (for example, 33 in FIG. 7) by using the MRI image (for example, the MRI image from which noise and holes are removed) segmented into the plurality of regions.

In step S240, the server 100 can generate the three-dimensional brain map configured with a plurality of meshes capable of simulating a delivery process of the electric stimulation based on the attributes of each of the plurality of regions included in the three-dimensional brain image generated through step S230. For example, the server 100 can generate a three-dimensional stereoscopic image configured with a plurality of volumetric meshes including a tetrahedron or a hexahedron, or can generate a three-dimensional stereoscopic image configured with a plurality of surface meshes including a triangle or a quadrangle, but the present invention is not limited thereto. The type of mesh constituting the three-dimensional stereoscopic image can be set differently according to the purpose of the simulation.

In step S250, the server 100 can simulate the electric stimulation for the plurality of stimulation positions based on the three-dimensional brain map configured with the plurality of meshes.

In various embodiments, the server 100 can generate the pre-computation information by previously computing some computation processes of the simulation in order to improve the efficiency of the simulation process, such as increasing the computation speed of the simulation, or the like and can simulate the electric stimulation for the plurality of stimulation positions by using the pre-computation information.

First, the server 100 can acquire physical properties of each of the plurality of regions for simulating the flow of current according to the electrical stimulation to the brain of the subject as pre-computation information.

Herein, the physical property may be electrical conductivity (for example, at least one of isotropic electrical conductivity and anisotropic electrical conductivity of each of the plurality of regions), but the present invention is not limited thereto.

In various embodiments, the server 100 can assign a known electrical conductivity through an experiment (for example, white matter 0.126 S/m, gray matter 0.276 S/m, cerebrospinal fluid 1.65 S/m, skull 0.01 S/m and skin 0.465 S/m) for each of the plurality of segmented regions.

In addition, the server 100 can acquire anisotropic electrical conductivity for each of the plurality of regions from the MRI image including a conduction tensor image for the brain of the subject. For example, the server 100 can acquire anisotropic electrical conductivity according to the direction of a nerve fiber included in a diffusion tensor image in consideration that eigenvectors of a diffusion tensor image coincide with eigenvectors of a conduction tensor.

After that, the server 100 can set one of the plurality of stimulation positions as the reference stimulation position and can perform the simulation while changing the remaining different stimulation positions except for the reference stimulation position among the plurality of stimulation positions based on the set reference stimulation position.

For example, the server 100 can calculate the coordinate system of the preset guide system (for example, 10-20 system) based on the head image of the subject. After that, the server 100 can perform the simulation by setting the reference stimulation position among the plurality of stimulation positions and configuring at least one stimulation position among the remaining stimulation positions (the remaining stimulation positions except for the reference stimulation position among the plurality of stimulation positions) and the set reference stimulation position as one stimulation position combination.

That is, the server 100 can acquire the stimulation result by determining the stimulation position combination including the one reference stimulation position and at least one stimulation position among the remaining different stimulation positions except for the reference stimulation position and performing the simulations for each stimulation position combination.

In various embodiments, the server 100 can arbitrarily select two or more stimulation positions among the plurality of stimulation position, and can acquire a stimulation result by performing the simulation for the arbitrarily selected two or more stimulation positions.

Herein, since the server 100 can simulate the electric stimulation based on the three-dimensional brain map configured with a plurality of meshes, the server 100 can simulate the stimulation for the plurality of stimulation positions by using at least one of a finite element method (FEM), a finite difference method (FDM), and a finite volume method (FVM) which are performing the simulation by using a three-dimensional model having a mesh structure, but the present invention is not limited thereto.

After that, the server 100 can derive a linear relationship for each of the plurality of stimulation positions as the pre-computation information for the simulation by using the simulation result generated by applying the electric stimulation to each of the plurality of stimulation positions according to the preset guide system.

For example, since the stimulation result collected by applying the electric stimulation to each of the plurality of stimulation positions has a linear characteristic, the server 100 can derive a linear relationship between the plurality of stimulation positions by using the stimulation result collected by applying the electric stimulation to each of the plurality of stimulation positions. For example, since the electric field and the current density due to the stimulation have a linear relationship with each other, a linear relationship as illustrated in Equation 1 below can be derived.

$$E(C1_a, C2_b, C3_{-a-b}) = E(C1_a, C3_{-a}) + E(C2_b, C3_{-b}) \quad \text{<Equation 1>}$$

Herein, $E(C1_a, C2_b)$ may be a brain current distribution when a and b currents are applied to C1, which is the first stimulation position and C2 which is the second stimulation position, respectively.

That is, a linear equation of the form Ax=E can be derived by using the linear relationship as in Equation 1 described above (where x is an amount of current applied to the stimulation position, E is the electric field value), a desired value of E, that is, an electric field value, can be linearly calculated by adjusting an x value.

Herein, the x value can be an M×1 matrix (where M is the number of stimulation positions (or electrodes) used in the simulation), E can be an N×1 matrix (where N is the number of nodes included in the three-dimensional brain map), and A can be an N×M matrix (where each column of the N×M matrix is a pre-computation result). That is, the server 100 can calculate the A matrix as a linear relationship for each of the plurality of stimulation positions, that is, pre-computation information.

In various embodiments, in a case where the number of the plurality of stimulation positions is n, the server 100 can derive a linear relationship for each of the plurality of stimulation positions by only (n−1) simulations. For example, in a case where the simulation is performed on a total of three stimulation positions (for example, a first stimulation position, a second stimulation position, and a third stimulation position), a linear relationship between the second stimulation position and the third stimulation position can be derived through a simulation result for the first stimulation position and the second stimulation position and a simulation result for the first stimulation position and the third stimulation position, and thus, the linear relationship for each of the three stimulation positions can be derived through only the two-times simulations for a total of three stimulation positions.

In various embodiments, the server 100 can filter the stimulation positions corresponding to the preset condition among the plurality of stimulation positions and can simulate the electric stimulation for the brain of the subject by using the remaining stimulation positions except for the filtered stimulation positions among the plurality of stimulation positions.

Hereinafter, the description will be made with reference to FIGS. 9 to 12.

Figure 9:
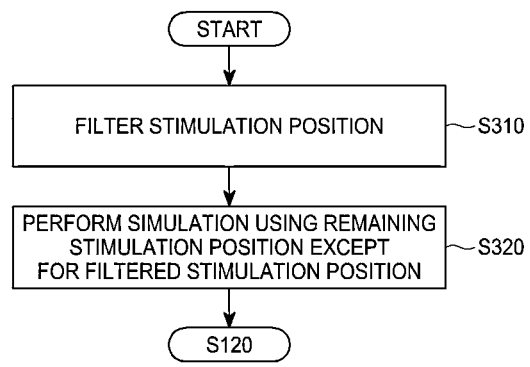
FIG. 9 is a flowchart illustrating a method for simulating electric stimulations by filtering stimulation positions in various embodiments.

FIG. 9 is a flowchart illustrating a method for simulating the electric stimulation by filtering the stimulation position in various embodiments.

Referring to FIG. 9, in step S310, the server 100 can filter the stimulation positions corresponding to the preset condition among the plurality of stimulation positions according to the preset guide system.

In various embodiments, the server 100 can filter at least one stimulation position by using the head image of the subject.

First, the server 100 can acquire the head image generated by imaging the head of the subject and can set one or more reference stimulation positions based on the acquired head image. For example, the server 100 can provide the first UI (for example, 50 in FIG. 12) to the user terminal 200, can output the plurality of stimulation positions according to the preset guide system through the first UI, can set the reference stimulation position by selecting one or more of the output stimulation positions as the reference stimulation position. However, the present invention is not limited thereto, and various methods such as a method for automatically setting the reference stimulation position for calculating the plurality of stimulation positions according to the preset guide system by image analysis of the head image of the subject can be applied.

After that, the server 100 can set the plurality of stimulation positions based on one or more reference stimulation positions. For example, in a case where the number of the reference stimulation positions set according to the above-mentioned method is a total of four and there are four stimulation positions (Nz, Iz, LPA, and RPA) corresponding to nasal muscle (Nasion), occipital pole (Inion), left pre-auricle (Left pre-auricular) and right pre-auricle (right pre-auricular) of the subject, the server 100 can calculate the point where the first connection line connecting the stimulation positions (Nz and Iz) corresponding to the nasal muscle and the laryngeal pole and the second connection line connecting the stimulation positions (LPA and RPA) corresponding to the left pre-auricle and the right pre-auricle intersects each other as the central coordinate and can derive the coordinate system for the plurality of stimulation positions according to the 10-20 system using the distance information on the first connection line and the second connection line based on the central coordinates. As an example, the server 100 can derive the coordinate system of the 10-20 system so that the first connection line and the second connection line are segmented by a distance of 10% or 20%, respectively, based on the central coordinates.

After that, the server 100 can set a filtering target region (for example, a standard region for filtering the stimulation position) by using the plurality of stimulation positions set on the head image and can filter at least one stimulation position based on the set filtering target region.

Figure 10:
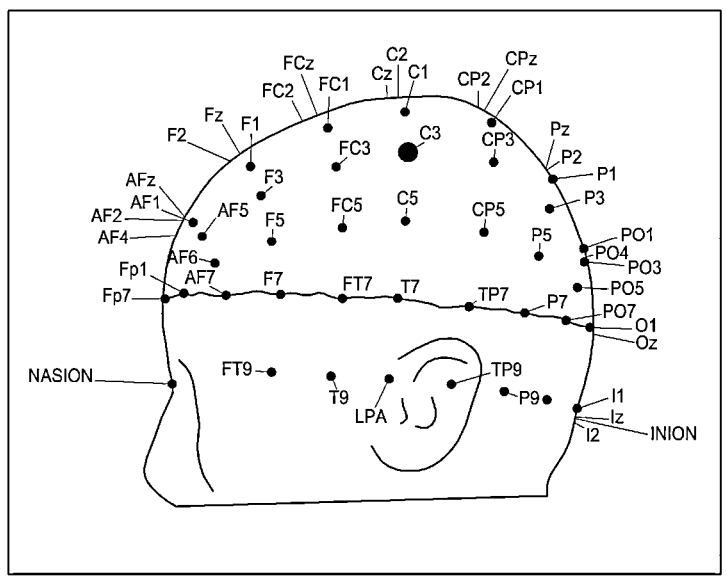
FIG. 10 is a diagram exemplarily illustrating a form of filtering at least one stimulation position by setting a filtering target region in various embodiments.

In various embodiments, the server 100 can set a plane including one or more reference stimulation positions as the filtering target region and can filter at least one stimulation position located on the plane set as the filtering target region based on the plane set as the filtering target region. For example, as illustrated in FIG. 10, in a case where one or more reference stimulation positions are four stimulation positions (Nz, Iz, LPA, and RPA) corresponding to each of the nasal muscles, the laryngeal pole, the left pre-auricle, and the right pre-auricle, the server 100 can set the plane including Nz, Iz, LPA, and RPA as the filtering target region and can filter all stimulation positions located on the plane including Nz, Iz, LPA, and RPA.

In various embodiments, the server 100 can filter all stimulation positions located at the bottom of the corresponding plane based on the plane set as the filtering target region. For example, in a case where one or more reference stimulation positions set by the user are Fpz, T7, Oz, and T10, the server 100 can filter Nz, Iz, LPA, RPA which are the stimulation positions located at the bottom of the plane including Fpz, T7, Oz, and T10.

In other words, the stimulation position corresponding to each of the nasal muscle, the laryngeal pole, the left pre-auricle, and the right pre-auricle is hard to attach the electrodes due to the shape of the head or the ears or the stimulation position is hard to attach the electrodes to the accurate position even if the electrodes are attached, and thus, in this embodiment, the stimulation position corresponding to the above-mentioned position can be filtered.

In various embodiments, the server 100 can analyze the head image, can detect the region in which the electrode attachment on the head of the subject is not possible, can set the detected region in which the electrode attachment is not possible as the filtering target region, and can filter at least one stimulation position included in the filtering target region. For example, in a case where there is an region with a metal substance (clip, coil, metabolic foreign body, or the like) in the brain of the subject, or there is an injury such as a scalp disease or wound, there is a problem in that it is difficult to apply the electric stimulation by attaching the electrodes to the region. In consideration of this point, the server 100 can detect the region where the electrode attachment is not possible as described above by analyzing the head image of the subject through image analysis and can filter the stimulation position included in the detected region.

In step S320, the server 100 can simulate the electric stimulation for the brain of the subject by using the remaining stimulation positions except for the filtered stimulation position among the plurality of stimulation positions. Herein, similarly to the above-mentioned method, the method for simulating the electric stimulation for the brain of the subject by using remaining stimulation positions except for the filtered stimulation positions can be performed by using at least one of the finite element method, the finite difference method, and the finite volume method as above.

In various embodiments, the server 100 can segment the brain of the subject into two regions, that is, into a left hemisphere region and a right hemisphere region and can perform the simulations for the left hemisphere region and the right hemisphere region individually.

Figure 11:
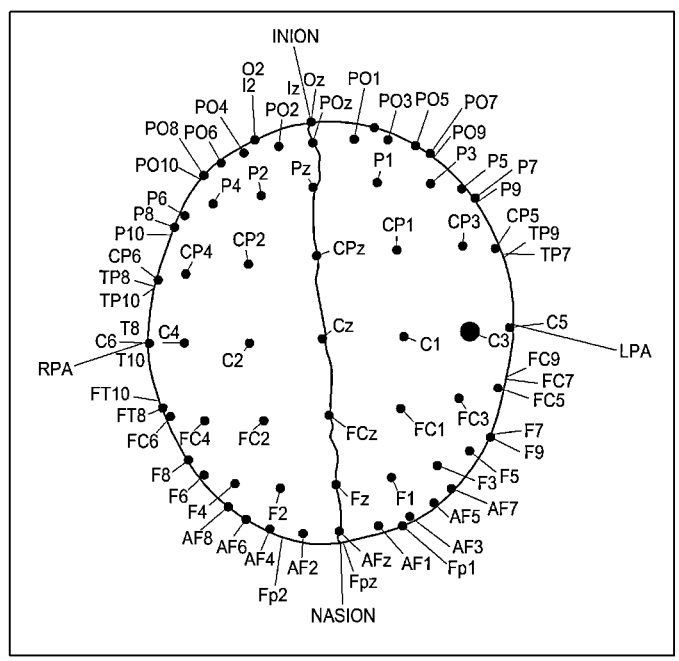
FIG. 11 is a diagram exemplarily illustrating a form in which a brain region of the subject is segmented into a left hemisphere region and a right hemisphere region according to various embodiments.

First, as illustrated in FIG. 11, the server 100 can segment the brain region of the subject into a left hemisphere region and a right hemisphere region by using a first geodesic line connecting the first stimulation position corresponding to the nasal muscle of the subject and the second stimulation position corresponding to the laryngeal pole, and a second geodesic line connecting the third stimulation position corresponding to the left pre-auricle and the fourth stimulation position corresponding to the right pre-auricle.

After that, the server (100) can select two or more stimulation positions located in the left hemisphere among the remaining stimulation positions except for the filtered stimulation position and simulate the electric stimulation for the left hemisphere of the brain of the subject or can select two or more stimulation positions located in the right hemisphere among the stimulation positions except for the remaining filtered stimulation position and simulate the electric stimulation for the right hemisphere region of the brain of the subject.

At this time, the server 100 can filter the stimulation position so that currents of different polarities are not applied to the same region. For example, in a case where any one stimulation position located on the left hemisphere region is selected, the server 100 can filter at least one stimulation position to which a current having a polarity opposite to that of the current applied to any one of the stimulation positions among other stimulation positions located on the left hemisphere region that is the same region as the selected one stimulation position (for example, the stimulation position to which a negative current is applied can be filtered in a case where a positive current is applied to any one of stimulation positions.

In addition, in a case where any one stimulation position located on the right hemisphere region is selected, the server 100 can filter at least one stimulation position to which a current having a polarity opposite to that of the current applied to any one of the stimulation positions among other stimulation positions located on the right hemisphere region that is the same region as the selected one stimulation position.

That is, the server 100 can exclude the case where the anode and the cathode are located in the same hemisphere in order to exclude the result in which clinical verification for safety is not made.

As described above, unnecessary calculations during the simulation can be reduced by filtering unnecessary stimulation positions in advance according to the preset conditions and performing the simulation by using only the remaining stimulation positions according to the filtered result.

Again, referring to FIG. 3, in step S120, in a case where any one stimulation position located on the right hemisphere region is selected, the server 100 can determine the optimal stimulation position combination for applying the electric stimulation to the preset target point in the brain of the subject based on the result of the electric stimulation simulation performed through step S110.

In various embodiments, the server 100 can calculate the optimal stimulation position by using a linear relationship for each of the plurality of stimulation positions generated as the pre-computation information.

Herein, the optimal stimulation position may denote the position to which the stimulation can be applied with maximum efficiency under a given condition (for example, region where the electrode can be located, output of the electrode, or the like) for the stimulation region suitable for a patient with a specific disease obtained by various clinical or theoretical studies.

This is similar to a method for finding a solution to an inverse problem that finds a condition for obtaining a desired result rather than obtaining a result according to a given condition, and a numerical optimization method can be used. The above-mentioned meaning of applying stimulation with maximum efficiency denotes a stimulation condition in which the electric field in a desired region is maximized as interpreted in terms of actual electromagnetic meaning, and thus, in order to obtain this stimulation condition, it is possible to derive a linear relationship between a specific stimulation applied to each of the plurality of stimulation positions and the electric fields output according to this from the result of performing the simulation of the electric stimulation and pre-computation information.

In various embodiments, the server 100 can derive a linear relationship between the electric fields output according to the application of a specific stimulation under an arbitrary stimulation condition as illustrated in Equation 2 below from the result of performing the simulation of the electric stimulation.

$$E_m(r) = \alpha B_m(r) \qquad \text{<Equation 2>}$$

Herein, E may be the electric field, r may be the coordinates of the stimulation position, m may be an arbitrary stimulation condition, a may be the ratio of the actual stimulation to the basic unit stimulation intensity, and B may be the basic unit stimulation intensity.

The electric field (E) that can be finally obtained according to Equation 2 is equal to a product of the basic unit stimulation intensity (B) of the stimulation and the ratio ($\alpha$) of the actual stimulation to the basic unit stimulation intensity, and with respect to the stimulation combination in the various stimulation positions in this manner, in a case where the stimulation is applied, the linear relationship between the two stimulations with different stimulation conditions can be expressed as Equation (3).

$$E \sum m_i(r) = \sum_{i=1}^{n} \alpha_i B_{m_i}(r) \qquad \text{<Equation 3>}$$

Herein, $m_i$ may be an i-th stimulation condition.

After that, the server 100 can derive a linear relationship between a combination of different stimulation conditions and an electric field output when the stimulation is applied according to the stimulation condition as in Equation 3.

Accordingly, since a linear system of equations for various stimulation conditions and desired stimulation intensity can be obtained, the server 100 can finally obtain the stimulation condition that the maximum stimulation can be applied to the desired stimulation position by using numerical optimization. Herein, a least square method, a weighted least square method, or an L1 norm constrained method can be applied, but the present invention is not limited thereto.

In various embodiments, the server 100 can calculate the optimal stimulation position for applying the electric stimulation to the preset target point in the brain of the subject by using the linear relationship according to Equation 3 described above. For example, since the desired result can be reversely known as the stimulation conditions including information on the target point in the brain of the subject is received as an input from the user, the server 100 can calculate the optimal stimulation position (for example, 41 of FIG. 8) to which the electric stimulation is applied and can determine the optimal stimulation position combination by configuring the calculated optimal stimulation position into as combination.

In various embodiments, the server 100 can correct the optimal stimulation position combination based on the number of maximum stimulation positions in which the electric stimulation is applied to the preset target point. Hereinafter, the description will be made with reference to FIG. 13.

Figure 13:
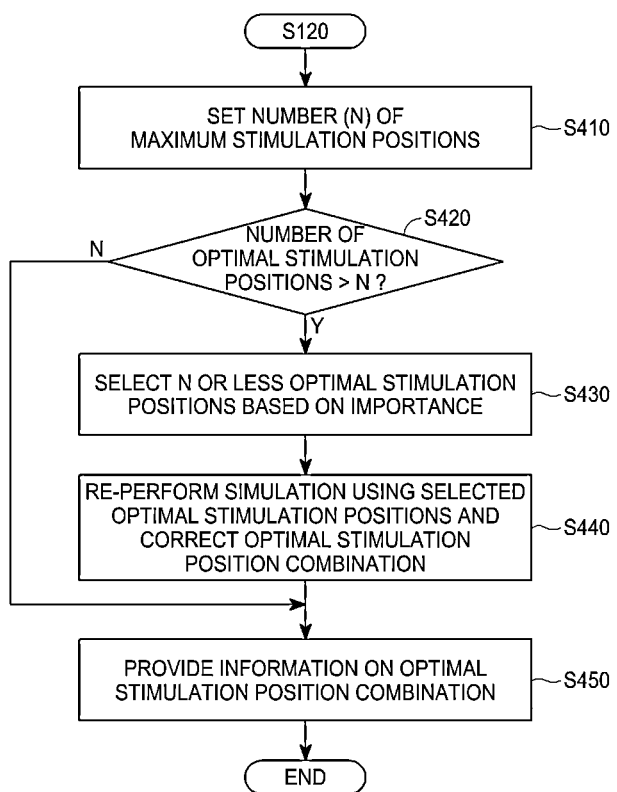
FIG. 13 is a flowchart illustrating a method for correcting the optimal stimulation position combination in accordance with limitation of the number of available electrodes in various embodiments.

FIG. 13 is a flowchart illustrating a method for correcting the optimal stimulation position combination in accordance with a limited number of available electrodes in various embodiments.

Referring to FIG. 13, in step S410, the server 100 can set the number of maximum stimulation positions in which the electric stimulation is applied to the preset target point. For example, the server 100 can provide the second UI (60 in FIG. 14) to the user terminal 200, and can receive the number of maximum stimulation positions through the first UI 60. However, the present invention is not limited thereto.

In step S420, the server 100 can determine whether the number of the plurality of optimal stimulation positions exceeds the number of maximum stimulation positions by comparing the number of the plurality of optimal stimulation positions included in the optimal stimulation position combination determined according to the above-mentioned method (for example, steps S110 and S120 in FIG. 3) and the number of the maximum stimulation positions set in step S410.

In step S430, in a case where it is determined that the number of the plurality of optimal stimulation positions exceeds the number of the maximum stimulation positions, the server 100 can select at least one (less than or equal to the number of maximum stimulation positions) of the plurality of optimal stimulation positions among the plurality of optimal stimulation positions based on the importance of each of the plurality of optimal stimulation positions.

In various embodiments, the server 100 can set the importance for each of the plurality of optimal stimulation positions based on the positions of the plurality of optimal stimulation positions and can select at least one optimal stimulation position among the plurality of optimal stimulation positions according to the set importance. For example, in a case where the subject to be applied with the electric stimulation is a patient with diseases such as epilepsy and brain diseases, there is an region where the electric stimulation cannot be applied according to diseases such as epilepsy and brain diseases. In consideration of this, in a case where there is a region where the electric stimulation cannot be applied according to the disease of the subject as described above the server 100 can calculate the distance between the region where the electric stimulation cannot be applied and each of the plurality of optimal stimulation positions and can perform setting so as to set high importance from the optimal stimulation position having a long distance based on the calculated distance.

In various embodiments, the server 100 can set the importance for each of the plurality of optimal stimulation positions based on the current intensity applied to each of the plurality of optimal stimulation positions and can select at least one optimal stimulation position among the plurality of optimal stimulation positions according to the set importance. For example, a low current intensity applied to a specific stimulation position through an electrode denotes that the amount of stimulation applied, that is, the effect on the stimulation is small, and thus, the server 100 can perform setting so as to sequentially set higher importance according to the order of increasing the current intensity applied to each of the plurality of optimal stimulation positions.

In step S440, the server 100 can re-perform the simulation for the brain of the subject by using only at least one optimal stimulation position selected through step S430 and can correct the determined optimal stimulation position combination based on the result of the re-performed simulation.

At this time, the server 100 can perform the simulation for at least one optimal stimulation position by using only the information on the at least one optimal stimulation position in the pre-computation information, that is, by using the only remaining computation information obtained by removing the information on the filtered optimal stimulation position according to importance in the pre-computation information.

Since the pre-computation information includes information on the linear relationship for all stimulation positions, there is a problem in that differences in current intensity etc. occur between a case where the simulation is performed by using information on all the stimulation positions and a case where the simulation is performed by using only information on the selected at least one optimal stimulation position.

In addition, in a case where only the information on a specific optimal stimulation position is selectively used without removing information on the filtered optimal stimulation position according to the importance from the pre-computation information, there is a problem in that an error that cannot physically occur (for example, the total sum of input currents is 1 and the total sum of the output currents is 0.9, or the like).

In consideration of this problem, the server 100 can remove the information on the linear relationship for each of the optimal stimulation positions filtered according to importance from the pre-computation information and can re-perform the simulation by using only the information on the linear relationship between at least one optimal stimulation position selected according to the importance.

Figure 15:
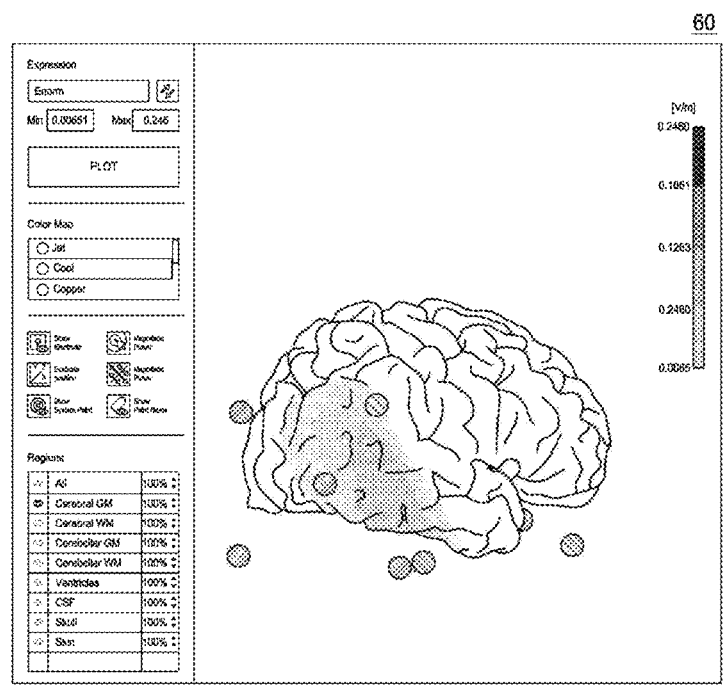

In step S450, the server 100 can determine the optimal stimulation position combination corrected through step S440 as the final optimal stimulation position combination, and can provide information on this to the user through the second UI 60 (for example, FIG. 15).

On the other hand, in a case where the number of the plurality of optimal stimulation positions is less than or equal to the number of maximum stimulation positions, at step S420, the server 100 can determine the determined optimal stimulation position combination as the final optimal stimulation position combination and can provide the information on this to the user through the second UI 60.

In various embodiments, the server 100 can standardize the current value applied to each of the plurality of optimal stimulation positions included in the optimal stimulation position combination determined according to the above-mentioned method according to the current resolution (the setting unit of the current value of a transcranial direct current stimulation (tDCS) device). Hereinafter, the description will be made with reference to FIGS. 16 to 18.

Figure 16:
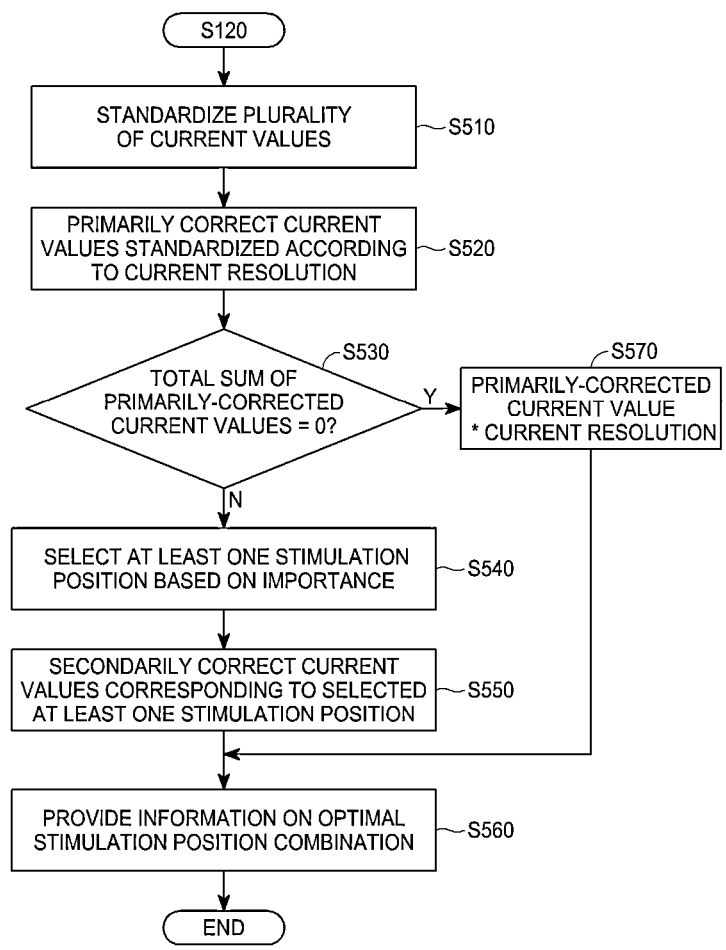
FIG. 16 is a flowchart illustrating a method for correcting current values to be applied to the stimulation positions according to the current resolution of a transcranial direct current stimulation (tDCS) device in various embodiments.

FIG. 16 is a flowchart illustrating a method for correcting the current value to be applied to the stimulation position according to the current resolution of the transcranial direct current stimulation (tDCS) device in various embodiments.

Referring to FIG. 16, in step S510, the server 100 can standardize the plurality of current values applied to each of the plurality of optimal stimulation positions included in the optimal stimulation position combination based on preset the current resolution. For example, the server 100 can provide the third UI (for example, 70 in FIG. 16) to the user terminal 200, can receive the current resolution input through the second UI 60, and can standardize the plurality of current values by dividing the plurality of current values applied to each of the plurality of optimal stimulation positions by the input the current resolution value.

In step S520, the server 100 can perform primary correction (for example, rounding up, rounding down, rounding off, or the like) on each of the plurality of current values standardized in step S510 so that each of the plurality of current values standardized in step S510 is a multiple of a preset resolution. For example, in a case where the current applied to the first optimal stimulation position is 220 mA and the preset current resolution is 200 mA, the server 100 can calculate the standardized current value of 1.1 obtained by dividing the current value applied to the first optimal stimulation position by the preset current resolution and can correct the standardized current value from 1.1 to 1 for the first optimal stimulation position by rounding off the calculated standardized current value so as to be a multiple of the preset current resolution (that is, the standardized current value has a natural number value such as 1, 2, and 3). In addition, in a case where the current applied to the second optimal stimulation position is 350 mA, the server 100 can calculate the standardized current value of 1.5 by dividing the current value applied to the second optimal stimulation position by the preset current resolution and can correct the standardized current value from 1.5 to 2 for the second optimal stimulation position by rounding off the calculated standardized current value by the preset current resolution.

In step S530, the server 100 can calculate the total sum of the plurality of primarily-corrected current values and can determine whether the total sum of the calculated plurality of primarily-corrected current values is 0.

In step S540, in a case where it is determined that the total sum of the plurality of primarily-corrected current values is not 0, the server 100 can select at least one optimal stimulation position among the plurality of optimal stimulation positions based on the importance of each of the plurality of optimal stimulation positions. Herein, a method for setting the importance of each of the plurality of optimal stimulation positions can be implemented in the same or similar form as the method for setting the importance performed in step S430 (for example, a method based on the optimal stimulation position and the current intensity applied to the optimal stimulation position). However, the present invention is not limited thereto.

Herein, the server 100 can determine the number of the optimal stimulation positions selected according to the magnitude of the total sum of the plurality of primarily-corrected current values. For example, in a case where the magnitude of the total sum of the plurality of primarily-corrected current values is 4 (as the standardized current value, the real current value is 800 mA) and the preset current resolution is 1 (as the standardized current value, the real current value is 200 mA), the server 100 can select a total of four optimal stimulation positions in order to correct the current value applied to the optimal stimulation position by 200 mA which is the current resolution. However, the present invention is not limited thereto.

In various embodiments, the server 100 can sequentially select at least one optimal stimulation position in order from the optimal stimulation position having a low importance based on the importance of each of the plurality of optimal stimulation positions set according to the above scheme (the position of the optimal stimulation position and the current intensity applied to the optimal stimulation position). For example, the server 100 can sequentially select the optimal stimulation positions in order from the optimal stimulation position having the lowest current intensity applied to each of the plurality of optimal stimulation positions.

In various embodiments, the server 100 can determine a method for selecting at least one optimal stimulation position according to the importance setting standard for each of the plurality of optimal stimulation positions.

As an example, in a case where the importance setting standard is the position of the plurality of optimal stimulation positions, the server 100 can sequentially select optimal stimulation positions in order from the optimal stimulation position having a low importance based on the set importance.

On the other hand, in a case where the importance setting standard is the current intensity applied to each of the plurality of optimal stimulation positions, the server 100 can sequentially select the optimal stimulation positions in order from the optimal stimulation position having a high importance based on the set importance.

In a case where the importance setting standard is the current intensity, as the current intensity becomes lower, the importance becomes lower. Therefore, in a case where the optimal stimulation positions are sequentially selected in order from the optimal stimulation position having a low importance, the optimal stimulation positions are selected in order from the optimal stimulation position having a low current intensity. Since the current value applied to the optimal stimulation position selected in this manner has a relatively low value, in case where the current value is corrected by the current resolution, the current value becomes very small, and thus, the influence of the electric stimulation is almost eliminated or the applied the current value is set to 0 in some cases. As a result, there is no influence in applying the electric stimulation to the target point. On the other hand, in the case of the optimal stimulation position in which the importance is set to be high, since the applied the current value is large, even if correction is performed by adding or subtracting as much as a magnitude of the current resolution, there is no significant influence in applying the electric stimulation to the target point. In consideration of this point, the server 100 can sequentially select the optimal stimulation positions in order from the optimal stimulation position having an importance set to be high in a case where the importance setting standard is the current intensity.

In step S550, the server 100 can correct the current values (primarily-corrected current values) corresponding to the at least one optimal stimulation position selected through step S540 so that the total sum of the plurality of primarily-corrected current values becomes 0. For example, in a case where the magnitude of the total sum of the plurality of primarily-corrected current values is 800 mA and the preset current resolution is 200 mA, and a total of four optimal stimulation positions are selected based on the importance, the server 100 can secondarily correct the current values by decreasing each the current value applied to each of the four optimal stimulation positions by 200 mA so that the total sum of the plurality of primarily-corrected current values is 0.

In step S560, the server 100 calculates the current value to be applied to each of the plurality of optimal stimulation positions by multiplying the plurality of current values secondarily-corrected through step S550 by the preset current resolution and can provide the information on the optimal stimulation position combination including the information on the optimal stimulation position and the information on the current value to be applied to each optimal stimulation position through the third UI 70 by using the calculated the current value (for example, FIG. 18).

In step S570, in a case where it is determined that the total sum of the plurality of primarily-corrected current values is 0 at step S530, the server 100 can calculate the current value to be applied to each of the plurality of optimal stimulation positions by multiplying each of the plurality of primarily-corrected current values by the preset current resolution and can provide the information on the optimal stimulation position combination including information on the calculated the current value.

The optimal stimulation position combination determination method using the preset guide system described above was described with reference to the flowchart illustrated in the drawings. For a simple description, the optimal stimulation position combination determination method using the preset guide system has been illustrated and described as a series of blocks, but the present invention is not limited to the order of the blocks, and some blocks may be performed in an order different from or simultaneously with those illustrated and operated in this specification.

In addition, the embodiments can be performed in a state where new blocks not described in the present specification and the drawings can be added, or some blocks can be deleted or changed.

In the above, embodiments of the present invention have been described with reference to the accompanying drawings, but the ordinarily skilled in the art to which the present invention belongs can understand that the present invention can be carried out in other specific forms without changing technical spirit or essential features. Therefore, it should be understood that the embodiments described above are illustrative in all respects and are not restrictive.

The invention claimed is:

1. An optimal stimulation position combination determination method performed by a computing device using a preset guide system to apply electric stimulation to a target point preset to a brain of a subject, comprising:
simulating the electric stimulation for the brain of the subject by using a plurality of stimulation positions according to the preset guide system; and
determining an optimal stimulation position combination for applying the electric stimulation to the preset target point based on a simulation result of the electric stimulation,
wherein the simulating the electric stimulation includes:
filtering stimulation positions corresponding to a preset condition among the plurality of stimulation positions; and
simulating the electric stimulation for the brain of the subject by using remaining stimulation positions except for the filtered stimulation positions among the plurality of stimulation positions.

2. The optimal stimulation position combination determination method according to claim 1,
wherein the simulating the electric stimulation includes:
generating a three-dimensional brain map corresponding to the brain of the subject; and
simulating the electric stimulation by using the plurality of stimulation positions based on the generated three-dimensional brain map.

3. The optimal stimulation position combination determination method according to claim 2,
wherein the generating the three-dimensional brain map includes:
acquiring an MRI image of the brain of the subject;
segmenting the acquired MRI image into a plurality of regions;
generating a three-dimensional brain image by using the MRI image segmented into the plurality of regions; and
generating the three-dimensional brain map configured with a plurality of meshes based on an attribute of each of the plurality of regions included in the generated three-dimensional brain image.

4. The optimal stimulation position combination determination method according to claim 2,
wherein the determining the optimal stimulation position combination includes:
setting the number of maximum stimulation positions at which the electric stimulation is applied to the preset target point, and
correcting the determined optimal stimulation position combination by comparing the number of the optimal stimulation positions included in the determined optimal stimulation position combination with the number of the set maximum stimulation positions.

5. The optimal stimulation position combination determination method according to claim 4,
wherein the correcting the determined optimal stimulation position combination includes:
selecting at least one of the plurality of optimal stimulation positions based on importance of each of the plurality of optimal stimulation positions, in a case where the number of the plurality of optimal stimulation positions included in the determined optimal stimulation position combination exceeds the number of the set maximum stimulation positions, wherein the number of the selected at least one optimal stimulation position is less than or equal to the number of the set maximum stimulation positions; and
simulating the electric stimulation by using only the selected at least one optimal stimulation position and correcting the determined optimal stimulation position combination based on a simulation result of the electric stimulation by using only the selected at least one optimal stimulation position.

6. The optimal stimulation position combination determination method according to claim 4, further comprising providing information on the determined optimal stimulation position combination in a case where the number of the plurality of optimal stimulation positions included in the determined optimal stimulation position combination is less than or equal to the number of the set maximum stimulation positions.

7. The optimal stimulation position combination determination method according to claim 1,
   wherein the determining the optimal stimulation position combination includes:
      standardizing a plurality of current values applied to each of the plurality of optimal stimulation positions included in the determined optimal stimulation position combination based on a preset current resolution;
      primarily correcting each of the plurality of standardized current values so that each of the plurality of standardized current values is a multiple of the preset current resolution; and
      secondarily correcting at least one current value of the plurality of primarily-corrected current values based on a total sum of the plurality of primarily-corrected current values.

8. The optimal stimulation position combination determination method according to claim 7,
   wherein the secondarily correcting includes:
      selecting at least one optimal stimulation position among the plurality of optimal stimulation positions based on importance of each of the plurality of optimal stimulation positions in a case where the total sum of the plurality of primarily-corrected current values is not 0 and determining the number of the selected at least one optimal stimulation positions according to a magnitude of the total sum of the plurality of primarily-corrected current values; and
      secondarily correcting the primarily-corrected current values corresponding to the selected at least one optimal stimulation position so that the total sum of the plurality of primarily-corrected current values is 0.

9. The optimal stimulation position combination determination method according to claim 7,
   wherein the determining the optimal stimulation position combination further includes:
      providing information on the determined optimal stimulation position combination including a value obtained by multiplying each of the plurality of primarily-corrected current values by the preset current resolution in a case where the total sum of the plurality of primarily-corrected current values is 0.

10. An optimal stimulation position combination determination server using a preset guide system, comprising:
    a processor;
    a network interface;
    a memory; and
    a computer program loaded on the memory and executed by the processor,
    wherein the computer program includes:
       an instruction of simulating electric stimulation for a brain of a subject by using a plurality of stimulation positions according to the preset guide system; and
       an instruction of determining an optimal stimulation position combination for applying the electric stimulation to a preset target point in the brain of the subject, based on a simulation result of the electric stimulation,
    wherein the instruction of simulating electric stimulation includes:
       an instruction of filtering stimulation positions corresponding to a preset condition among the plurality of stimulation positions; and
       an instruction of simulating the electric stimulation for the brain of the subject by using remaining stimulation positions except for the filtered stimulation positions among the plurality of stimulation positions.

11. A computer program recorded on a tangible, non-transitory, computer-readable recording medium,
    combined with a computing device, and
    causing the computing device to execute:
       simulating electric stimulation for a brain of a subject by using a plurality of stimulation position according to a preset guide system; and
       determining an optimal stimulation position combination for applying the electric stimulation to the preset target point in the brain of the subject by using a simulation result of the electric stimulation,
    wherein the simulating the electric stimulation includes:
       filtering stimulation positions corresponding to a preset condition among the plurality of stimulation positions; and
       simulating the electric stimulation for the brain of the subject by using remaining stimulation positions except for the filtered stimulation positions among the plurality of stimulation positions.

* * * * *